(12) United States Patent
Casugbo et al.

(10) Patent No.: US 9,889,079 B2
(45) Date of Patent: Feb. 13, 2018

(54) PROCESS FOR MAKING A CONDITIONING GEL PHASE

(71) Applicant: Conopco, Inc., Englewood Cliffs, NJ (US)

(72) Inventors: Christia Casugbo, New Ferry (GB); Mark Flanagan, Chester (GB); John Alan Hough, Neston (GB); John Michael Naughton, Wallasey (GB); David Serridge, Bromborough (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/416,173

(22) PCT Filed: Jul. 24, 2013

(86) PCT No.: PCT/EP2013/065646
§ 371 (c)(1),
(2) Date: Jan. 21, 2015

(87) PCT Pub. No.: WO2014/016352
PCT Pub. Date: Jan. 30, 2014

(65) Prior Publication Data
US 2015/0216775 A1 Aug. 6, 2015

(30) Foreign Application Priority Data

Jul. 27, 2012 (EP) .................................... 12178167
Aug. 3, 2012 (EP) .................................... 12179303

(51) Int. Cl.
*A61K 8/42* (2006.01)
*A61K 8/41* (2006.01)
*A61K 8/04* (2006.01)
*A61K 8/34* (2006.01)
*A61Q 5/12* (2006.01)

(52) U.S. Cl.
CPC ................. *A61K 8/42* (2013.01); *A61K 8/04* (2013.01); *A61K 8/042* (2013.01); *A61K 8/342* (2013.01); *A61K 8/416* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 4,726,945 A | 2/1988 | Patel | |
| 6,479,041 B2 | 11/2002 | Huff | |
| 6,544,500 B1 | 4/2003 | O'Toole et al. | |
| 8,530,399 B2 | 9/2013 | Giles et al. | |
| 8,828,370 B2 | 9/2014 | Yang et al. | |
| 2003/0185779 A1 | 10/2003 | Mitsumatsu | |
| 2005/0013789 A1* | 1/2005 | Sakai | A61K 8/342 424/70.21 |
| 2006/0078527 A1 | 4/2006 | Midha | |
| 2007/0104672 A1 | 5/2007 | Decoster et al. | |
| 2007/0128147 A1 | 6/2007 | Schwartz et al. | |
| 2007/0286837 A1 | 12/2007 | Torgerson et al. | |
| 2009/0041711 A1 | 2/2009 | Molenda | |
| 2009/0324528 A1* | 12/2009 | Okada | A61K 8/042 424/70.27 |
| 2015/0150763 A1 | 6/2015 | Casugbo | |
| 2015/0209254 A1 | 7/2015 | Casugbo | |
| 2015/0238402 A1 | 8/2015 | Casugbo | |

FOREIGN PATENT DOCUMENTS

| | | |
|---|---|---|
| CN | 1572280 | 2/2005 |
| CN | 102448427 | 5/2012 |
| EP | 0149180 A2 | 7/1985 |
| EP | 1491180 A1 | 12/2004 |
| EP | 2460508 | 6/2012 |
| JP | 2005255627 | 9/2005 |
| JP | 2005343860 | 12/2005 |
| JP | 2008515921 | 5/2008 |
| JP | 2009534395 | 9/2009 |
| JP | 2010013405 | 1/2010 |
| JP | 2010509262 | 3/2010 |
| JP | 2011525540 | 9/2011 |
| RU | 2027769 | 1/1995 |
| RU | 2315137 | 1/2008 |
| RU | 83250 | 5/2009 |
| RU | 136044 | 12/2013 |
| SU | 1312482 | 5/1987 |
| SU | 1641902 | 4/1991 |
| WO | WO9962467 A1 | 12/1999 |
| WO | WO9962492 A1 | 12/1999 |
| WO | WO2007019160 | 2/2007 |
| WO | WO2007136708 A2 | 11/2007 |
| WO | WO2008055816 | 5/2008 |
| WO | WO2010136285 A1 | 12/2010 |
| WO | WO2014016353 | 3/2014 |

OTHER PUBLICATIONS

IPRP2 in PCT2013065647, dated Dec. 12, 2013, pp. 1-15.
Seach Report in EP12178165, dated Dec. 12, 2013, pp. 1-15.
Search Report in EP12178167, dated Apr. 24, 2013, pp. 18-19.
Search Report in EP12178168, dated Jan. 14, 2013, pp. 20-21.
Search Report in EP12178171, dated Jan. 14, 2013, pp. 22-23.
Search Report in PCTEP2013065644, datedDec. 12, 2013, pp. 24-31.
Search Report in PCTEP2013065645, dated Apr. 23, 2014, pp. 32-35.
Search Report in PCTEP2013065646, dated Apr. 23, 2014, pp. 36-39.
Search Report in PCTEP2013065647, dated Dec. 12, 2013, pp. 40-43.

(Continued)

*Primary Examiner* — Ernst V Arnold
*Assistant Examiner* — Kyung Sook Chang
(74) *Attorney, Agent, or Firm* — Karen E. Klumas

(57) ABSTRACT

Process for making a conditioning gel phase comprising: i) forming an aqueous dispersion of fatty alcohol and amidoamine; ii) adding a cationic surfactant to the aqueous dispersion and mixing; and iii) neutralizing the amidoamine, wherein the temperature of the mixture of cationic surfactant in the aqueous dispersion is maintained at from 56° C. to 67° C.

14 Claims, No Drawings

(56) References Cited

OTHER PUBLICATIONS

Search Report in PCTEP2013065648, dated Dec. 12, 2013, pp. 44-47.
Written Opinion in EP12178165, dated Apr. 24, 2013, pp. 1-4.
Written Opinion in EP12178167, dated Apr. 24, 2013, pp. 5-7.
Written Opinion in EP12178168, dated Jan. 14, 2013, pp. 8-10.
Written Opinion in EP12178171, dated Jan. 14, 2013, pp. 11-13.
Written Opinion in PCTEP2013065644, dated Dec. 12, 2013, pp. 14-23.
Written Opinion in PCTEP2013065645, dated Apr. 23, 2014, pp. 24-30.
Written Opinion in PCTEP2013065646, dated Apr. 23, 2014, pp. 31-36.
Written Opinion in PCTEP2013065647, dated Dec. 12, 2013, pp. 37-41.
Written Opinion in PCTEP2013065648, dated Dec. 12, 2013, pp. 42-46.
Co-pending Application: Applicant: Casugbo et al., Filed: Jan. 21, 2015.
Evans, Evalutating Hair Conditioning with Instrumental Combing, Cosmetics & Toiletries, Aug. 1, 2011, pp. 1-5.
Written Opinion in EP13741742 dated Aug. 19, 2016.

\* cited by examiner

PROCESS FOR MAKING A CONDITIONING GEL PHASE

The present invention relates to a process for manufacturing improved conditioner compositions.

WO 99/62467 (P&G) and WO 99/62492 (P&G) disclose a method for manufacturing a conditioning composition by forming a conditioning gel phase by melting fatty alcohol with tertiary amidoamine and cationic surfactant.

WO 2007/019160 (Alberto Culver) discloses a process for making a conditioning gel phase comprising adding fatty alcohol to stearamidopropyl dimethyl amine and cationic surfactant.

Despite the prior art there remains a need for improved conditioning compositions.

Accordingly, and in a first aspect, there is provided a process for making a conditioning gel phase according to claim 1.

Conditioning compositions made with the conditioning gel phase of the invention have improved conditioning performance. More specifically, the conditioning compositions made using the conditioning gel phase of the invention are thicker, even when using a lower level of solids, and provide improved clean feel the following day. This is surprising since one usually associates improved conditioning with increased deposition of solids which results on greasiness and heaviness the next day. To provide the opposite is an unmet consumer need.

Preferably, the temperature of the aqueous dispersion is maintained above the melting temperature of the fatty alcohol, preferably at least 5° C. higher than the melting point of the fatty alcohol.

Preferably, the aqueous dispersion is formed by adding fatty alcohol to water heated and maintained at least the melting point of the fatty alcohol and preferably at least 5° C. above the melting point of the fatty alcohol. Preferably, the aqueous dispersion is maintained at a melting point sufficient to maintain the fatty alcohol in a liquid phase.

Preferably, the temperature of the mixture of the aqueous dispersion is controlled such that it is maintained from 56-67° C., preferably from 58-65° C., more preferably 63° C.

Preferably, the temperature of the mixture of the aqueous dispersion and the cationic surfactant is maintained at from 56° C. to 67° C. More preferably, the temperature of the mix of the aqueous dispersion and the cationic surfactant is maintained at from 58° C. to 65° C.; most preferably at 63° C.

Controlling the temperature of the mixture of fatty alcohol and the cationic surfactant means controlling the formation of gel structure. In this process the temperature of the mixture of comelt and water is controlled by modifying the temperature/rate of the cationic surfactant to the fatty alcohol and an amidoamine surfactant aqueous mix. If too cold or too hot then a system having a mixture of structures results and this has poorer conditioning capability.

After formation of the gel phase further water and additional ingredients may be added in one go or it may be staged.

Preferably, the process is a batch process.

Preferably the mixing of the cationic surfactant with the aqueous dispersion is monitored by measurement of viscosity, such that when the viscosity change plateaus, the required degree association has occurred and then the amidoamine is neutralised. Typically, this mixing of the cationic surfactant and aqueous dispersion takes from 20 to 60 minutes.

The conditioning composition ultimately made using such conditioning gel phase has improved conditioning performance compared with an identical conditioning composition made with an identical formulation made using a standard process.

Preferably, the process comprises passing the contents of the mixture vessel through a mixer with rotor tip speed of 10-34, preferably from 21-27 and especially preferably 24 ms-1.

Preferably the aqueous dispersion comprises from 25 wt. % to 50 wt. %, more preferably from 35 to 45 wt. % of the total dispersion water.

Preferably the aqueous dispersion comprises from 4 to 20 wt. % of the total dispersion fatty alcohol.

Preferably the aqueous dispersion comprises from 1 to 5 wt. % of the total dispersion amidoamine.

Preferably the neutraliser added to the aqueous dispersion and cationic surfactant comprises sufficient neutraliser to neutralise at least 90 wt % of the cationic surfactant, more preferably at least 95% of the cationic surfactant, most preferably at least 99% of the cationic surfactant.

Preferably, the fatty alcohol comprises from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is particularly preferable.

The level of fatty alcohol in the conditioner of the invention (not just the conditioning gel phase) will generally range from 0.01 to 10%, preferably from 0.1% to 8%, more preferably from 0.2% to 7%, most preferably from 0.3% to 6% by weight of the composition. The weight ratio of cationic surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

Suitable conditioning surfactants include those selected from cationic surfactants, used singly or in admixture. Preferably, the cationic surfactants have the formula $N^+R^1R^2R^3R^4$ wherein $R^1$, $R^2$, $R^3$ and $R^4$ are independently ($C_1$ to $C_{30}$) alkyl or benzyl. Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl. More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (eg, oleyl). Alkyl groups are optionally ethoxylated on the alkyl chain with one or more ethyleneoxy groups.

Suitable cationic surfactants for use in the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Preferably, the cationic surfactant component of the comelt comprises from 0-70% cationic component, cationic surfactants have the formula $N^+R^1R^2R^3R^4$ as described above, more preferably from 30-60% wt. cationic surfactant component.

Suitable amidoamine surfactants (cationic when protoated) are preferably of the general formula (I):

$$R1CONH(CH2)mN(R2)R3 \quad (I)$$

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4. Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyl-diethylamine, palmitamidoethyldiethylamine, palmitamidoethyldimethylamine, behenamidopropyldimethyl-amine, behenamidopropyldiethylmine, behenamidoethyldiethylamine, behenamidoethyldimethylamine, arachidamidopropyl-dimethylamine, arachidamidopropyldiethylamine, arachid-amidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia, Pa., USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton, N.J., USA).

Acid may be any organic or mineral acid which is capable of protonating the amidoamine in the conditioner composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof. Particularly preferred is lactic acid.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate more than 95 mole % (293 K) of the amidoamine present.

Should an amidoamine of the type described herein be present then the corresponding acid component will not be present in the comelt. Instead it will be present in the water. Preferably, the water comprises protonating component at from 0.01 to 3% wt.

In conditioning compositions of the invention (not merely the conditioning gel phase), the level of cationic surfactant will generally range from 0.01% to 10%, more preferably 0.05% to 7.5%, most preferably 0.1% to 5% by weight of the composition.

In a second aspect there is provided a process for manufacturing a conditioning composition by forming a conditioning gel phase obtained by the first aspect and then adding any remaining ingredients. Typical remaining ingredients include fragrances, silicones, fibre actives or other benefit agents.

Preferably, the conditioning composition is passed through a mixer with rotor tip speed of 10-34, preferably from 21-27 and especially preferably 24 ms-1 one more time after the remaining ingredients have been added.

Suitable mixers for use with the invention have a kw/kg figures preferably in the range from 2 to 30 kw/kg, more preferably 10-25 and even more preferably 15-25.

Conditioning compositions of the invention or using conditioning gel phases of the invention also deposit silicone better than conventionally made conditioning compositions.

Accordingly, the compositions of the invention can contain, emulsified droplets of a silicone conditioning agent, for enhancing conditioning performance.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have an average silicone droplet size in the composition of less than 30, preferably less than 20, more preferably less than 10 micron, ideally from 0.01 to 1 micron. Silicone emulsions having an average silicone droplet size of 0.15 micron are generally termed microemulsions.

Emulsified silicones for use in the conditioner compositions of the invention will typically have a size in the composition of less than 30, preferably less than 20, more preferably less than 15. Preferably the average silicone droplet is greater than 0.5 micron, more preferably greater than 1 micron, ideally from 2 to 8 micron.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in shampoos and conditioners of the invention are amino functional silicones. By "amino functional silicone" is meant a silicone containing at least one primary, secondary or tertiary amine group, or a quaternary ammonium group. Examples of suitable amino functional silicones include polysiloxanes having the CTFA designation "amodimethicone".

Specific examples of amino functional silicones suitable for use in the invention are the aminosilicone oils DC2-8220, DC2-8177 and DC2-8566 (all ex Dow Corning).

Suitable quaternary silicone polymers are described in EP-A-0 530 974. A preferred quaternary silicone polymer is K3474 ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The total amount of silicone is preferably from 0.01 wt % to 10% wt of the total composition more preferably from 0.1 wt % to 5 wt %, most preferably 0.5 wt % to 3 wt % is a suitable level.

EXAMPLES

| Material | Active Level | A | 1 |
|---|---|---|---|
| Stearylamidopropyl dimethylamine | 100 | 1.25 | 1 |
| Behentrimonium Chloride | 70 | 1.25 | 1 |
| Lactic Acid | 88 | 0.38 | 0.285 |
| Cetearyl Alcohol | 100 | 5 | 4 |
| Parfum | 100 | 0.6 | 0.6 |
| Preservative | 55 | 0.1 | 0.1 |
| Disodium EDTA | 100 | 0.1 | 0.1 |
| Preservative | 1.5 | 0.04 | 0.04 |
| Potassium Chloride | 100 | 0.1 | 0.1 |
| PEG-150 distearate | 100 | 0.025 | 0 |
| Dimethicone/amodimethicone/Cetrimonium Chloride | 70 | 3.57 | 3.57 |
| Water | | To 100 | To 100 |

Formulation A is made by standard prior art process which mixes the fatty alcohol and water at 70 C. In contrast formulation 1 is made by adding a stearylamidopropyl dimethylamine and fatty alcohol to water at 60° C., maintain temperature by use of external heating, and stir.

Add a cationic surfactant, typically behentrimonium chloride, to this mixture, maintain temperature at 60° C. by use of external heating or cooling, and stir.

Add lactic acid to protonate stearylamidopropyl dimethylamine, maintain temperature at 60° C. by use of external heating or cooling, and stir.

Cool this towards ambient by adding more water, and other ambient temperature ingredients, and use of external cooling if required, and stir.

The compositions have different levels of conditioning active to demonstrate the improved conditioning performance of the composition made by the claimed process. Levels indicated are of raw materials.

| Panel data | A | 1 |
|---|---|---|
| Conditioner Attribute | | |
| Con Thickness | 58.28 C | 71.04 AB |
| Level Condition | 65.33 C | 69.72 AB |
| Overall Styling | 66.37 BC | 69.81 AB |
| Next Day | | |
| ND frizz | 18.39 a | 16.63 ab |
| ND clean feel | 65.86 B | 71.99 A |
| ND conditioning | 63.15 b | 68.45 a |

Panel data with approx 75 panelists, normal hair (mix of straight and wavy). Assessment via line scale.

The data shows that using a better process we have a thicker product despite having lower total solids (i.e. FA and BTAC). The ingredients are being used more efficiently.

In addition, the product is both significantly more conditioning than the control as well as feeling significantly more clean next day—unusual because there is usually a trade off (more conditioning=heavier) again, despite having a lower level of solids, i.e. conditioning active. One would have expected that a composition which provided improved conditioning benefits immediately post application would achieve this through increased deposition. However, if this were the case, the next day benefits would be markedly reduced.

The invention claimed is:
1. Process for making a conditioning gel phase comprising:
   i) forming an aqueous dispersion of fatty alcohol and amidoamine, wherein the temperature of the aqueous dispersion is maintained at least 5° C. above the melting point of the fatty alcohol;
   ii) adding a cationic surfactant to the aqueous dispersion and mixing, and
   iii) neutralising the amidoamine by the addition of acid, wherein:
      the amidoamine is of the general formula:

      $R^1CONH(CH_2)_mN(R^2)R^3$, wherein $R^1$ is a hydrocarbyl residue having from about 11 to about 24 carbon atoms, $R^2$ and $R^3$ are independently methyl or ethyl groups and m is 2 or 3,
      the fatty alcohol is C16 to C22 fatty alcohol, and
      the cationic surfactant is selected from the group of: cetyltrimethylammonium chloride, behenyltrimethylammonium chloride, cetylpyridinium chloride, tetramethylammonium chloride, tetraethylammonium chloride, octyltrimethylammonium chloride, dodecyltriethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, PEG-2-oleammonium chloride, and mixtures of any of the foregoing, wherein the temperature of the mixture of cationic surfactant in the aqueous dispersion of the fatty alcohol and amidoamine is maintained at from 56° C. to 67° C., and above the melting point of the fatty alcohol, for from 20 to 60 minutes, after which time the acid is added.

2. The process according to claim 1 in which the aqueous dispersion comprises from 4 to 20 wt % of the dispersion fatty alcohol.

3. The process according to claim 1 in which the aqueous dispersion comprises from 1 to 5 wt % of the dispersion amidoamine surfactant.

4. The process according to claim 1 in which the mixture of cationic surfactant and fatty alcohol and amidoamine comprises from 0.5 to 5 wt % cationic surfactant.

5. The process according, to claim 1 in which the cationic surfactant is behenyltrimethylammonium chloride.

6. The process according to claim 1 in which the amidoamine surfactant is stearylamidopropyl dimethylamine.

7. The process according to claim 1 in which the fatty alcohol is a C16 to C18 fatty alcohol.

8. The process according to claim 1 comprising passing the resulting conditioning gel phase through a mixer with rotor tip speed of 10-34 ms−1.

9. The process according to claim 1 wherein one or more additional ingredients selected from the group consisting of fragrances, silicones, fibre actives and other benefit agents are added after the conditioning gel phase is formed to produce a conditioning composition for hair treatment.

10. The process according to claim 1 wherein the temperature of the mixture of cationic surfactant in the aqueous dispersion of the fatty alcohol and amidoamine is maintained at from 58° C. to 85° C., and above the melting point of the fatty alcohol, for from 20 to 60 minutes, after which time the acid is added.

11. The process according to claim 9 comprising passing the conditioning composition through a mixer with rotor tip speed of 10-30 ms−1.

12. The process according to claim 1 wherein the cationic surfactant is cetyltrimethylammonium chloride and/or behenyltrimethylammonium chloride and the amidoamine is selected from the group consisting of stearamidopropyldimethylamine stearamidopropyldiethylamine, stearamidoethyldiethylamine, stearamidoethyldimethylamine, palmitamidopropyldimethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof.

13. The process according to claim 1 wherein the cationic surfactant is cetyltrimethylammonium chloride and/or behenyltrimethylammonium chloride.

14. The process according to claim 13 wherein the fatty alcohol is C16 to C18 fatty alcohol and the amidoamine is stearamidopropyldimethylamine.

* * * * *